US009164025B2

(12) United States Patent
Tasi et al.

(10) Patent No.: US 9,164,025 B2
(45) Date of Patent: Oct. 20, 2015

(54) METHOD FOR INSPECTION OF IMAGE STICKING

(71) Applicant: DAXIN MATERIALS CORP., Taichung (TW)

(72) Inventors: Min-Ruei Tasi, Kaohsiung (TW); Li-Hsin Chang, Taichung (TW); Chih-Chun Hsu, Taichung (TW); Kuan-Ming Lin, Taichung (TW)

(73) Assignee: Daxin Materials Corp., Taichung (TW)

( * ) Notice: Subject to any disclaimer, the term of this patent is extended or adjusted under 35 U.S.C. 154(b) by 72 days.

(21) Appl. No.: 13/858,540

(22) Filed: Apr. 8, 2013

(65) Prior Publication Data
US 2013/0278934 A1    Oct. 24, 2013

(30) Foreign Application Priority Data

Apr. 19, 2012 (TW) .............................. 101113955 A

(51) Int. Cl.
G01N 21/17    (2006.01)
G02F 1/13     (2006.01)
G02F 1/00     (2006.01)
G02F 1/1337   (2006.01)
G02F 1/1333   (2006.01)

(52) U.S. Cl.
CPC .......... G01N 21/1717 (2013.01); G02F 1/0045 (2013.01); G02F 1/1309 (2013.01); G02F 1/1337 (2013.01); G02F 2001/133397 (2013.01)

(58) Field of Classification Search
CPC ................. G02F 2001/133397; G02F 1/0045; G02F 1/1309; G02F 1/1337; G01N 21/1717

USPC ......................................... 356/434, 432, 433
See application file for complete search history.

(56) References Cited

U.S. PATENT DOCUMENTS

2003/0118752 A1*  6/2003  Choi et al. .................... 428/1.26
2010/0271744 A1  10/2010  Ni et al.
(Continued)

FOREIGN PATENT DOCUMENTS

JP       10306281 A  * 11/1998  ............. C09K 19/30
JP    2004335871 A    11/2004
(Continued)

OTHER PUBLICATIONS

Masanobu Mizusaki, Tetsuya Miyashita, Tatsuo Uchida, Yuichiro Yamada, and Yutaka Ishii, the Mechanism of Image Sticking on LCD and its Evaluation Parameters Related to LC and Alignment Materials, Jun. 2006, SID Symposium Digest of Technical Papers, vol. 37, Issue 1, pp. 673-676, Jun. 2006, DOI: 10.1889/1.2433596.*

Primary Examiner — Michael A Lyons
Assistant Examiner — Violeta A Prieto
(74) Attorney, Agent, or Firm — McNees Wallace & Nurick LLC

(57) ABSTRACT

A method for image sticking inspection of a light-transmissive device is disclosed. The light-transmissive device is responsive to application of a voltage to electrodes thereof to adjust light transmission characteristics. The method includes: providing light for passage through the light-transmissive device; applying a first alternating current (AC) voltage to the electrodes; applying a direct current voltage to the electrodes; and applying a second AC voltage to the electrodes, and measuring intensity of the light passing through the light-transmissive device during application of the second AC voltage.

3 Claims, 9 Drawing Sheets

(56) References Cited

U.S. PATENT DOCUMENTS

2010/0277179 A1* 11/2010 Mizusaki et al. .............. 324/459
2011/0222005 A1* 9/2011 Mizusaki et al. .............. 349/123
2012/0121291 A1   5/2012 Tsuji et al.

FOREIGN PATENT DOCUMENTS

| JP | 2006133379 A | 5/2006 |
| JP | 2009192759 A | 8/2009 |
| JP | 2009294364 A | 12/2009 |

* cited by examiner

METHOD FOR INSPECTION OF IMAGE STICKING

CROSS-REFERENCE TO RELATED APPLICATION

This application claims priority to Taiwanese Application No. 101113955, filed on Apr. 19, 2012.

BACKGROUND OF THE INVENTION

1. Field of the Invention

The invention relates to a method and a system for inspection, and more particularly to a method and a system for image sticking inspection.

2. Description of the Related Art

A liquid crystal display (LCD) panel includes two substrates, two alignment layers, a liquid crystal layer, a plurality of electrodes, and a circuit. The circuit applies voltage to the electrodes of the LCD panel to adjust light transmittance at different regions of the LCD panel. However, the LCD panel may encounter image sticking as a result of poor circuit design or inappropriate materials being used therein.

A conventional method for image sticking inspection used by a panel manufacturer includes: displaying a checkerboard pattern using the LCD panel for a long time period, and inspecting severity of image sticking using human eyes.

Another method for image sticking inspection is disclosed in Japanese patent application publication no. 2009-294364, which includes the following steps:

providing light to the LCD panel;

applying an alternating current (AC) voltage to the electrodes of the LCD panel using the circuit thereof, such that each region of the LCD panel has a transmittance of 50%, and measuring intensity of the light passing through each region of the LCD panel;

applying a load voltage to the electrodes of the LCD panel using the circuit thereof, such that the LCD panel displays the checkerboard pattern; and applying the AC voltage to the electrodes of the LCD panel using the circuit thereof, such that each region of the LCD panel has a transmittance of 50%, and measuring intensity of the light passing through each region of the LCD panel.

The severity of image sticking of the LCD panel can then be evaluated according to the measured intensity of the light.

However, the conventional method has the following drawbacks:

1. Even though the image sticking of the LCD panel may be evaluated as being serious, the root cause is not known to be as a result of poor circuit design or inappropriate materials being used.

2. The LCD panel must display the checkerboard pattern for a long time (about 168 hours) that is sufficient for appearance of the image sticking.

3. The LCD panel is composed of a thin-film transistor substrate and a color filter substrate. Each of the substrates is produced through 4 or 5 processes, resulting in a longer time requirement and a higher cost for image sticking inspection.

SUMMARY OF THE INVENTION

Therefore, an object of the present invention is to provide a method for image sticking inspection that can overcome the above drawbacks of the prior art.

According to one aspect of the present invention, there is provided a method for image sticking inspection of a light-transmissive device. The light-transmissive device is responsive to application of a voltage to electrodes thereof to adjust light transmission characteristics of the light-transmissive device. The method comprises:

a) providing light for passage through the light-transmissive device;

b) applying a first alternating current (AC) voltage to the electrodes of the light-transmissive device;

c) applying a direct current (DC) voltage to the electrodes of the light-transmissive device after step b); and d) applying a second AC voltage to the electrodes of the light-transmissive device after step c), and measuring intensity of the light passing through the light-transmissive device during application of the second AC voltage.

Another object of the present invention is to provide a system for image sticking inspection that can overcome the above drawbacks of the prior art.

According to another aspect of the present invention, there is provided a system for image sticking inspection of a light-transmissive device. The light-transmissive device is responsive to application of a voltage to electrodes thereof to adjust light transmission characteristics of the light-transmissive device. The system comprises:

a light source operable to provide light for passage through the light-transmissive device;

a driver to be coupled to the light-transmissive device, and operable to apply the voltage to the electrodes of the light-transmissive device, the voltage being a first alternating current (AC) voltage during a first time period, a direct current (DC) voltage during a second time period following the first time period, and a second AC voltage during a third time period following the second time period; and a light detector for measuring intensity of the light that is provided by the light source and that passes through the light-transmissive device.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
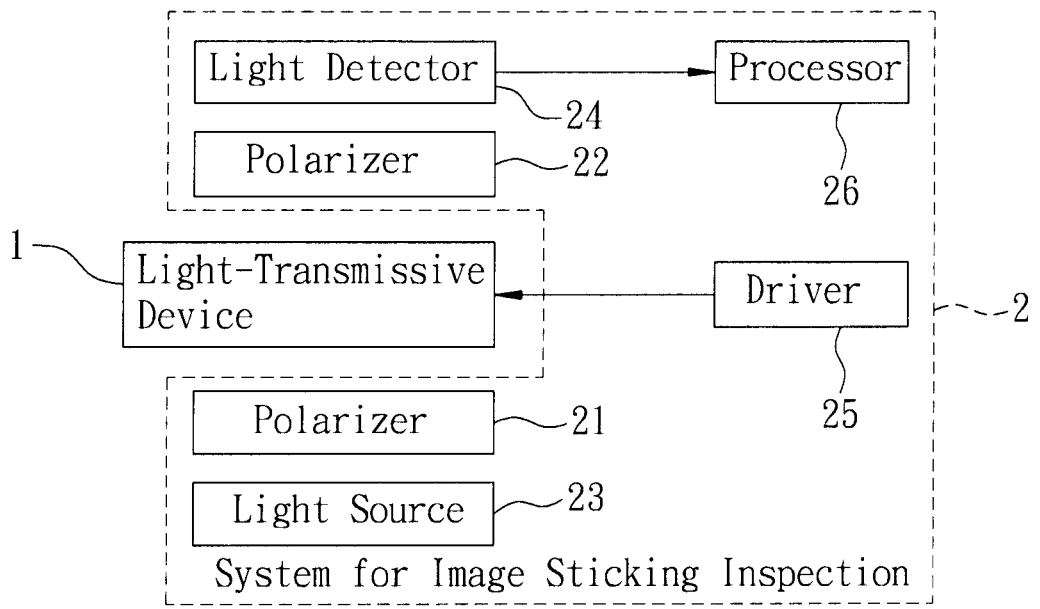
FIG. 1 is a block diagram illustrating a preferred embodiment of the system for image sticking inspection of a light-transmissive device according to the present invention.
Figure 2:
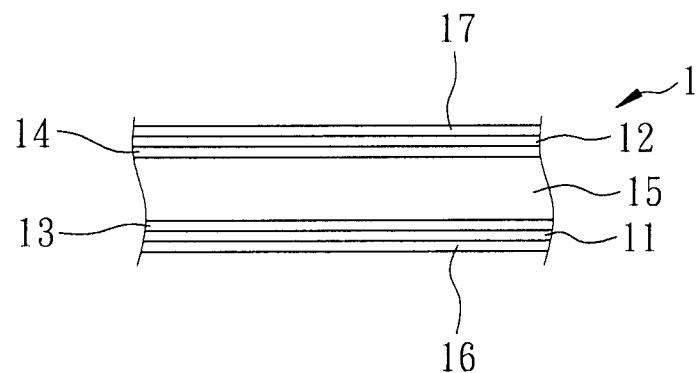
FIG. 2 is a schematic diagram showing the light-transmissive device for use with the preferred embodiment.

Referring to FIG. 1 and FIG. 2, the preferred embodiment of the system 2 for image sticking inspection of a light-transmissive device 1 according to this invention is shown.

The light-transmissive device 1 used in this embodiment includes two substrates 11, 12 spaced apart from each other, two alignment layers 13, 14 disposed respectively on the substrates 11, 12 and facing each other, a liquid crystal layer 15 disposed between the alignment layers 13, 14, and two electrodes 16, 17 disposed respectively on the substrates 11, 12 and opposite to each other. Each of the electrodes 16, 17 has a rated voltage not smaller than 10 volts. The light-transmissive device 1 is responsive to application of a voltage to the electrodes 16, 17 thereof to adjust light transmission characteristics of the light-transmissive device 1 in a known manner.

The system 2 of this embodiment includes two aligned polarizers 21, 22, a light source 23, a light detector 24, a driver 25, and a processor 26. The polarizers 21, 22 are spaced apart from each other so that the light-transmissive device 1 may be disposed therebetween. The light source 23 is operable to provide light for passage through the light-transmissive device 1 and the polarizers 21, 22. The light detector 24 is for measuring intensity of the light that is provided by the light source 23 and that passes through the light-transmissive device 1 and the polarizers 21, 22. The driver 25 is coupled to the light-transmissive device 1, and is operable to apply the voltage to the electrodes 16, 17 of the light-transmissive device 1. The processor 26 is coupled to the light detector 24 for obtaining various relations according to the light intensity measured by the light detector 24, and for generating plots according to the obtained relations.

Figure 3:
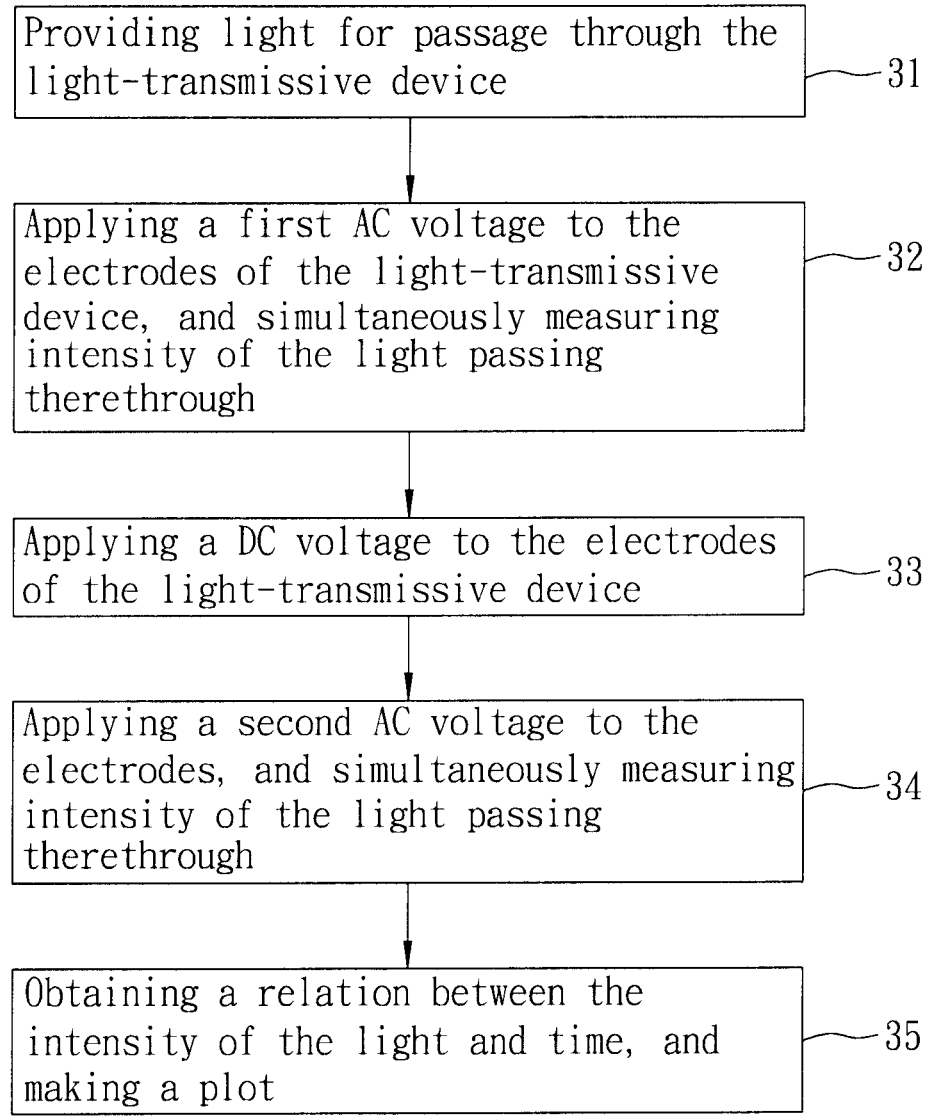
FIG. 3 is a flow chart illustrating steps of a first preferred embodiment of the method for image sticking inspection according to the present invention.

Further referring to FIG. 3, a first preferred embodiment of the method for image sticking inspection of the light-transmissive device 1 according to the present invention is shown to include the following steps 31~35, and is implemented using the system 2.

Step 31: The light source 23 provides light for passage through the light-transmissive device 1 and the polarizers 21, 22.

Step 32: The driver 25 applies a first alternating current (AC) voltage to the electrodes 16, 17 of the light-transmissive device 1, and the light detector 24 continuously measures the intensity of the light passing through the light-transmissive device 1 and the polarizers 21, 22 during application of the first AC voltage.

Figure 4:
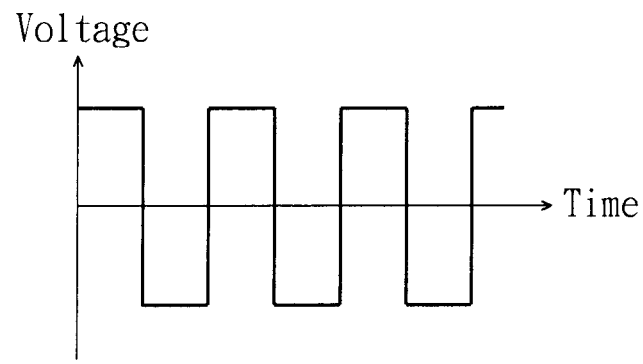
FIG. 4 is a timing diagram showing a first alternating current (AC) voltage applied in the first preferred embodiment.

In this embodiment, the first AC voltage has a constant peak voltage as shown in FIG. 4, such that a transmittance through the light transmissive device 1 and the polarizers 21, 22 is controlled to be substantially 50%. The first AC voltage has a frequency of 60 Hz, and is applied for a first time period of a multiple of 10 seconds, such as 20 seconds. However, the parameters are not limited to the values listed herein.

Step 33: The driver 25 applies a direct current (DC) voltage to the electrodes 16, 17 of the light-transmissive device 1 after step 32. The DC voltage has a magnitude not less than 10 volts, such that the transmittance through the light transmissive device 1 and the polarizers 21, 22 is controlled to be larger than that corresponding to the first AC voltage. Preferably, the magnitude of the DC voltage is not greater than 50 volts, and is applied for a second time period ranging between 1 minute and 20 minutes.

Step 34: The driver 25 applies a second AC voltage to the electrodes 16, 17 of the light-transmissive device 1 after step 33, and the light detector 24 continuously measures intensity of the light passing through the light-transmissive device 1 and the polarizers 21, 22 during application of the second AC voltage.

In this embodiment, the second AC voltage has a peak voltage and a frequency substantially equal to those of the first AC voltage and is applied for a third time period not less than 900 seconds. However, the parameters are not limited to the values listed herein.

Step 35: The processor 26 obtains a relation between the intensity of the light and time according to at least the intensities measured in step 34, and makes a plot according to the obtained relation.

Figure 5:
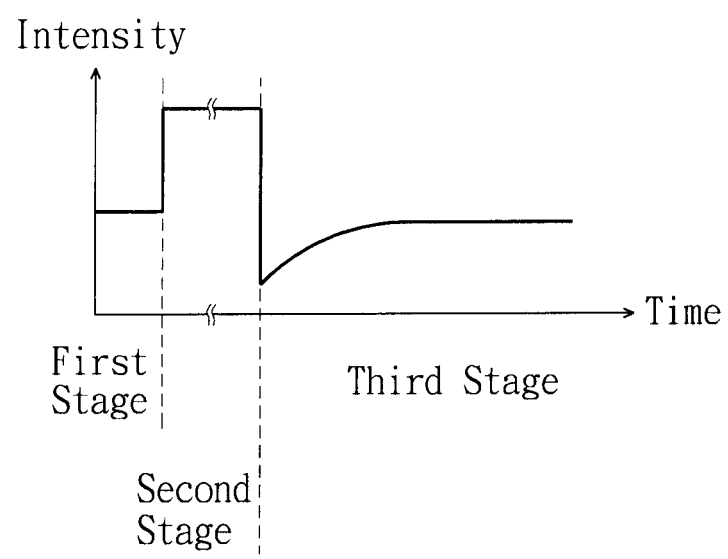
FIG. 5 is a timing diagram showing a light intensity variation related to the first preferred embodiment.
Figure 6:
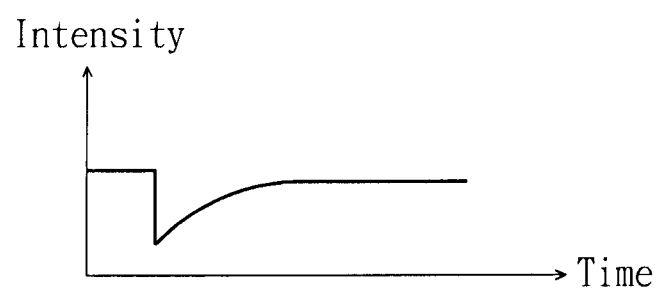
FIG. 6 is a timing diagram showing a light intensity variation related to the first preferred embodiment.

In this embodiment, the light received by the light detector 24 may have a relation between the intensity and time as shown in FIG. 5. The relation is divided into a first stage corresponding to step 32, a second stage corresponding to step 33, and a third stage corresponding to step 34. Therefore, the plot made by the processor 26 according to the intensity of light of the first and third stages is as shown in FIG. 6. The severity of image sticking of the light-transmissive device 1 may be evaluated according to the plot generated in step 35.

The first preferred embodiment has advantages as follows.

1. The light-transmissive device 1 being inspected has no circuits to control light transmission characteristics, so that when image sticking of the light-transmissive device 1 is evaluated to be serious according to the plot generated using the embodiment, it is known that the image sticking results from the materials used in the light-transmissive device 1. Therefore, the embodiment is suitable for inspection in the early development stage of the alignment layers and the liquid crystal layer, and makes it relatively easy to clarify the issue of whether a material is appropriate or not.

2. Since the maximum voltage applied by a circuit of a LCD panel is less than 10 volts, generally 7 volts, the LCD panel must display the checkerboard pattern for a relatively long time when using the conventional method for image sticking inspection. In this embodiment, by application of the DC voltage larger than 10 volts to the light-transmissive device 1, which is capable of receiving a DC voltage larger than 10 volts, the second time period may be reduced, thereby shortening the time required for inspection.

In addition, since the light-transmissive device 1 does not need to have the circuit during inspection, the substrates 11, 12 do not have to be the thin-film transistor substrate and the color filter substrate, thereby reducing inspection time and cost associated therewith.

Figure 7:
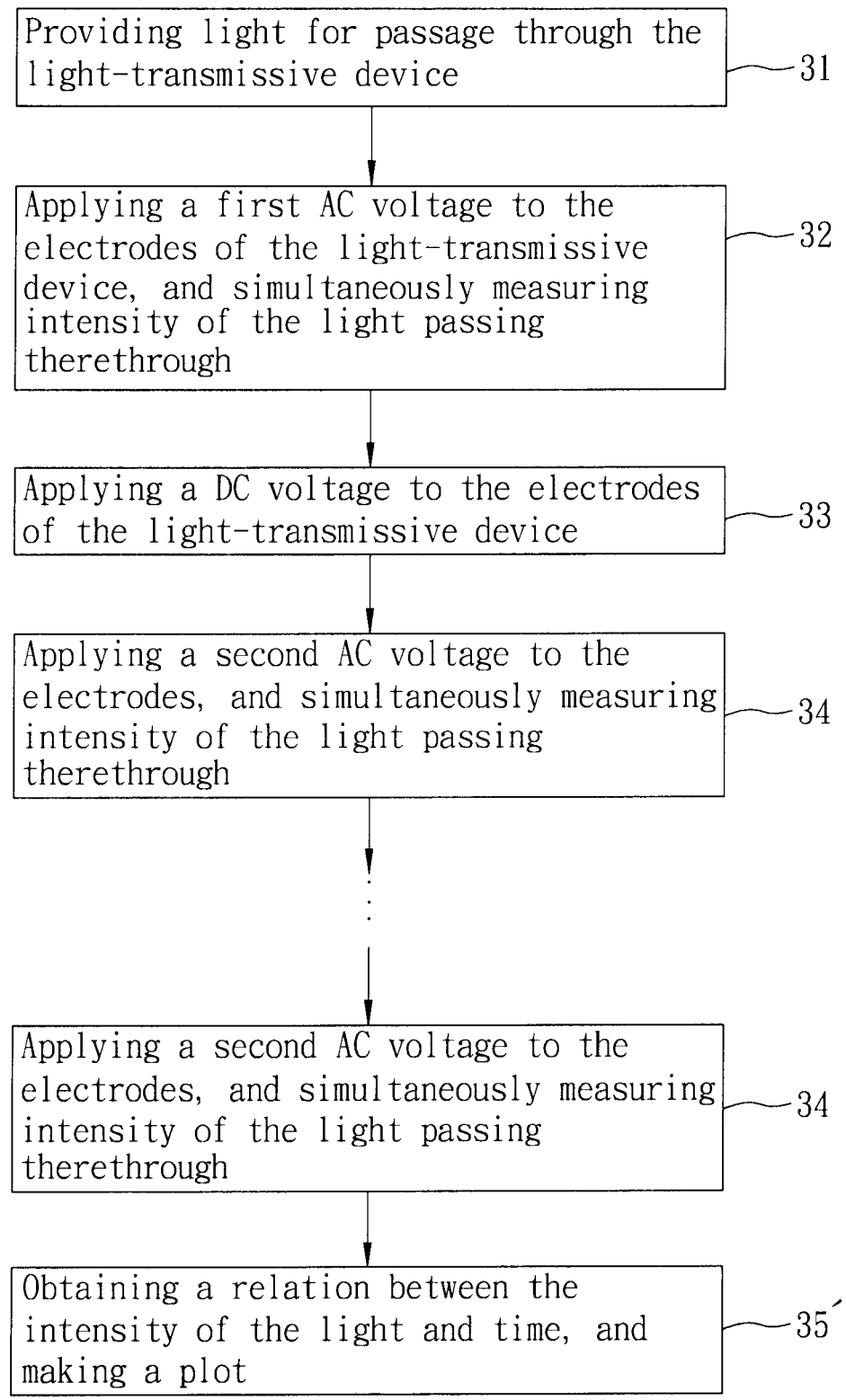
FIGS. 7 and 8 are flow charts illustrating steps of a second preferred embodiment of the method for image sticking inspection according to the present invention.
Figure 8:
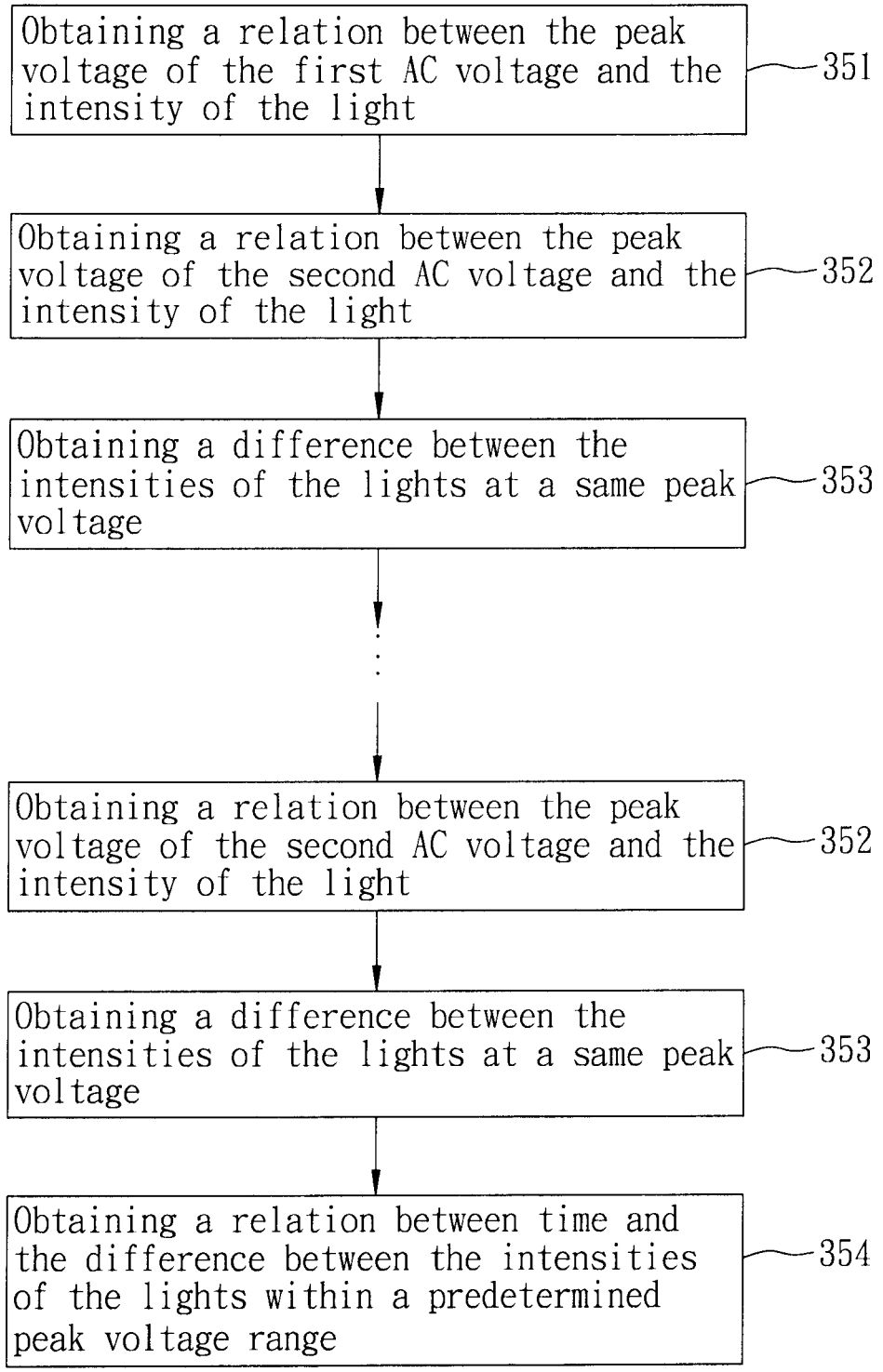
Figure 9:
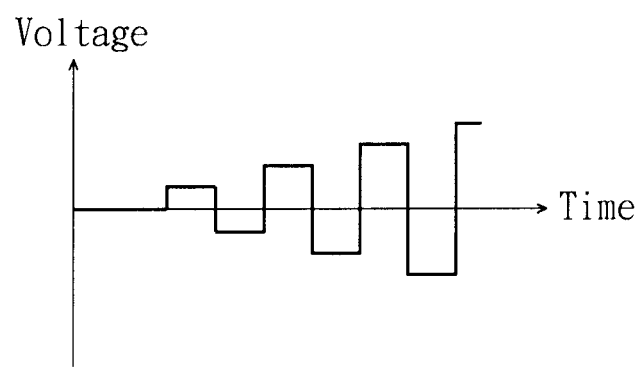
FIG. 9 is a timing diagram showing first and second AC voltages applied in the second preferred embodiment.

Referring to FIGS. 2, 7, and 8, a second preferred embodiment of the method for image sticking inspection of the light-transmissive device 1 is shown to be similar to the first preferred embodiment. The differences from the first preferred embodiment are illustrated as follows:

1. Both peak voltages of the first and second AC voltages increase with time, as shown in FIG. 9, such that the transmittance through the light-transmissive device 1 and the polarizers 21, 22 increase from 0% to 100% with time. In this embodiment, the peak voltages of the first and second AC voltages increase from 0 volt to 7 volts, at 1 volt increments. However, the parameters are not limited to the values listed herein. It should be noted that the peak voltages of the first and second AC voltages may vary with time in a different manner, such as to decrease with time.

2. Step 34 is repeated for a predetermined number of times, and for each repetition, the second time period is the same as the first time period. Preferably, there is a predetermined time interval between each repetition of step 34.

3. Step 35' includes the following sub-steps 351~355.

Figure 10:
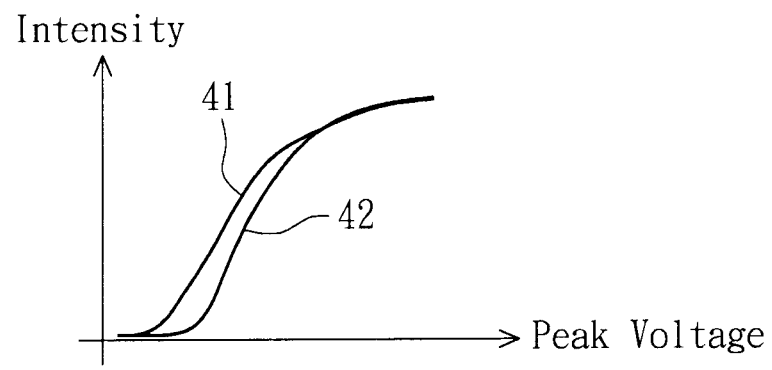
FIG. 10 is a plot showing a relation between a peak voltage and a light intensity related to the second preferred embodiment.

Step 351: The processor 26 obtains a relation between the peak voltage of the first AC voltage and the intensity of the light based on the intensity measured in step 32, as shown by a curve 41 in FIG. 10.

Step 352: The processor 26 obtains a relation between the peak voltage of the second AC voltage and the intensity of the light based on the intensity measured in step 34, as shown by a curve 42 in FIG. 10.

Figure 11:
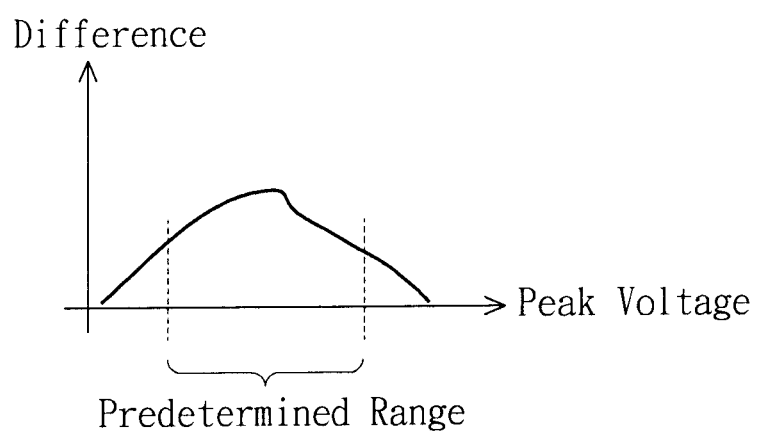
FIG. 11 is a plot showing a relation between the peak voltage and an intensity difference related to the second preferred embodiment.

Step 353: The processor 26 obtains a difference between the intensities of the lights at a same peak voltage from the relations obtained in steps 351 and 352, as shown in FIG. 11. Step 352 and step 353 are then repeated once for each repetition of step 34.

Figure 12:
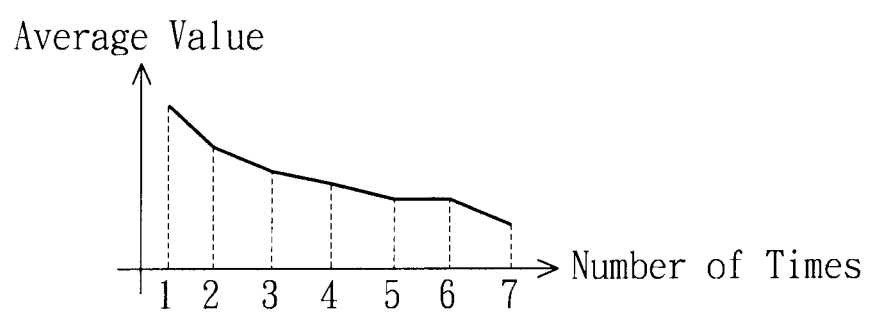
FIG. 12 is a plot showing a relation between an average value of intensity differences and time related to the second preferred embodiment.

Step 354: The processor 26 obtains a relation between time and the difference between the intensities of the lights within a predetermined peak voltage range obtained from each repetition of step 353. In this embodiment, the predetermined peak voltage range is between 2 volts and 4 volts, and an average value is obtained from 20 differences of the intensities in the peak voltage range of 2 volts to 4 volts for each repetition of step 353. A plot according to the average values thus obtained is then generated as shown in FIG. 12.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for image sticking inspection of a light-transmissive device, the light-transmissive device being responsive to application of a voltage to electrodes thereof to adjust light transmission characteristics of the light-transmissive device, said method to be implemented by a system including a light source, a driver coupled to the light-transmissive device, and a light detector, said method comprising:
   a) providing, by the light source, light for passage through the light-transmissive device;
   b) applying, by the driver, a first alternating current (AC) voltage to the electrodes of the light-transmissive device;
   c) applying, by the driver, a direct current (DC) voltage to the electrodes of the light-transmissive device after step b), the DC voltage having a magnitude not less than 10 volts;
   d) applying, by the driver, a second AC voltage to the electrodes of the light-transmissive device after step c), and measuring, by the light detector, intensity of the light passing through the light-transmissive device during application of the second AC voltage;

wherein:
   each of the first and second AC voltages has a peak voltage that varies in relation with time;
   step b) further includes continuously measuring the intensity of the light passing through the light-transmissive device during application of the first AC voltage; and
   in step d), the intensity of the light passing through the light-transmissive device during application of the second AC voltage is continuously measured, and step d) is repeated more than once;
said method further comprising:
   e) obtaining a relation between the peak voltage of the first AC voltage and the intensity of the light based on the intensity measured in step b);
   f) obtaining a relation between the peak voltage of the second AC voltage and the intensity of the light based on the intensity measured in step d);
   g) obtaining a difference between the intensities of the lights at a same peak voltage from the relations obtained in steps e) and f);
   h) repeating steps f) and g) for each repetition of step d); and
   i) obtaining a relation between time and the difference between the intensities of the lights within a predetermined peak voltage range obtained from each repetition of step g).

2. The method as claimed in claim 1, wherein, in step c), the DC voltage has a magnitude not greater than 50 volts.

3. The method as claimed in claim 1, wherein, in step c), the DC voltage is applied for a time period ranging from 1 minute to 20 minutes.

* * * * *